United States Patent [19]

Distler

[11] 4,004,784
[45] Jan. 25, 1977

[54] MACHINE FOR PREPARING ORTHOPEDIC CAST-MAKING MATERIALS

[75] Inventor: Edward C. Distler, Warminster, Pa.

[73] Assignee: Reichhold Chemicals, Inc., White Plains, N.Y.

[22] Filed: Aug. 14, 1975

[21] Appl. No.: 604,499

Related U.S. Application Data

[63] Continuation of Ser. No. 536,243, Dec. 24, 1974, abandoned.

[52] U.S. Cl. .................. 259/72; 118/53; 118/418; 259/81 R
[51] Int. Cl.² .......................................... B01F 9/00
[58] Field of Search ............ 259/3, 14, 30, 72, 73, 259/81 R; 118/6, 52, 53, 418

[56] References Cited

UNITED STATES PATENTS

| | | | |
|---|---|---|---|
| 2,824,029 | 2/1958 | Zinty | 118/53 |
| 2,946,273 | 7/1960 | Hitzl | 259/73 |
| 3,046,157 | 7/1962 | Nyman | 259/72 |
| 3,429,797 | 2/1969 | Jackson et al. | 118/418 |
| 3,706,443 | 12/1972 | Oberhauser | 259/72 |
| 3,880,408 | 4/1975 | Karjalainen | 259/72 |

Primary Examiner—Richard E. Aegerter
Assistant Examiner—Richard R. Stearns
Attorney, Agent, or Firm—Brooks Haidt Haffner & Delahunty

[57] ABSTRACT

Machine for sequentially rotating and tilting a container having materials therein for wetting or impregnating a tape to be used for forming an orthopedic cast, the machine having a turntable rotatable about a horizontal axis, a platform on the turntable for receiving the container base and rotatable about an axis transverse to the turntable axis and a clamp on the turntable for clamping the container on the platform. The turntable is rotatable by a first motor and the platform is rotatable by a second motor mounted on the turntable. The first and second motors are sequentially energized by a motor driven timing means to (a) tilt the container from its upright position to a position 45° from the vertical, (b) intermittently spin the container, (c) invert the container, (d) spin the container, (e) return the container to its upright position and (f) spin the container. To eliminate slip rings for energizing the second motor the turntable is rotated in opposite directions in steps (a) and (e) by a rack and gear drive between the first motor and the turntable.

13 Claims, 8 Drawing Figures

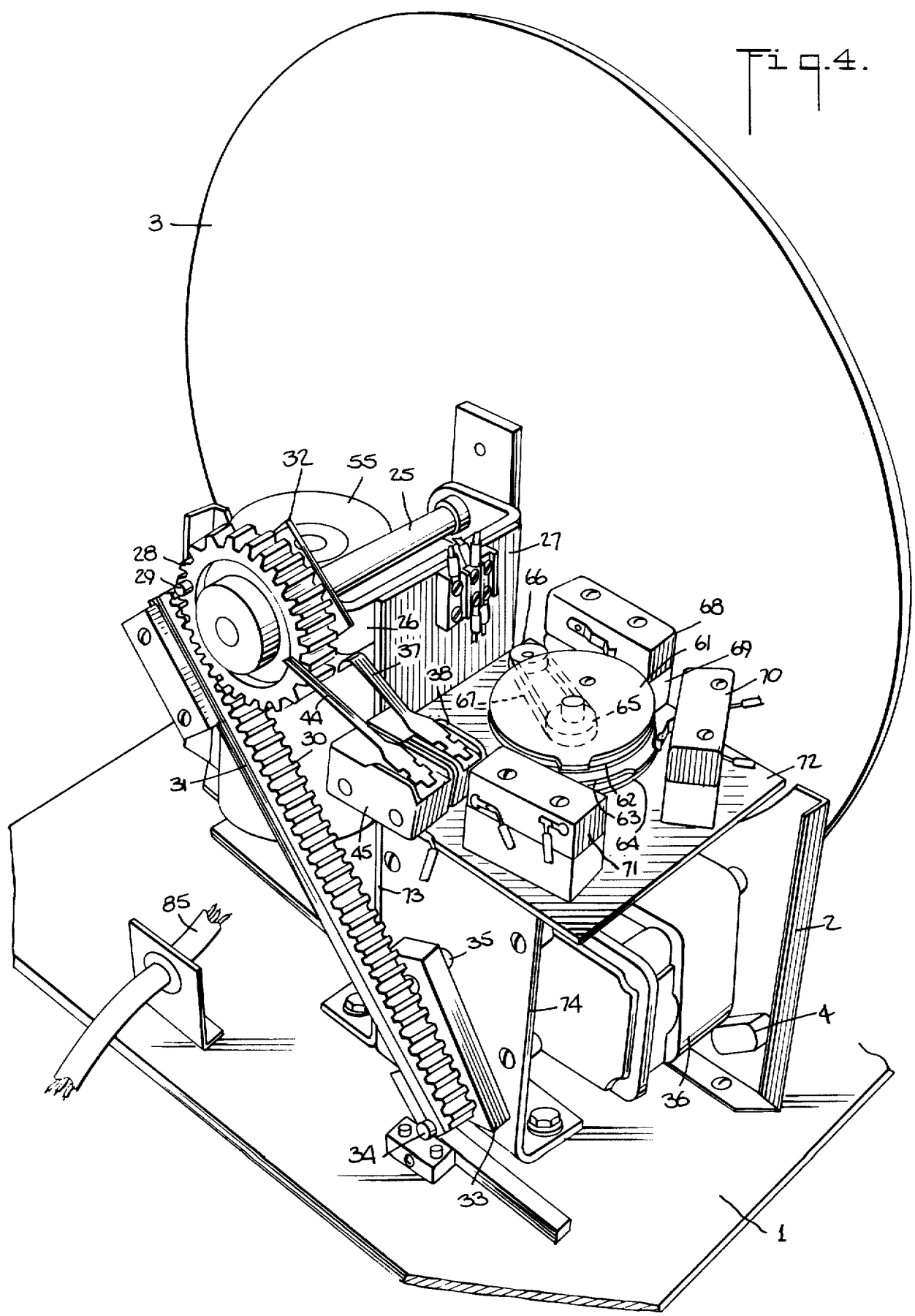

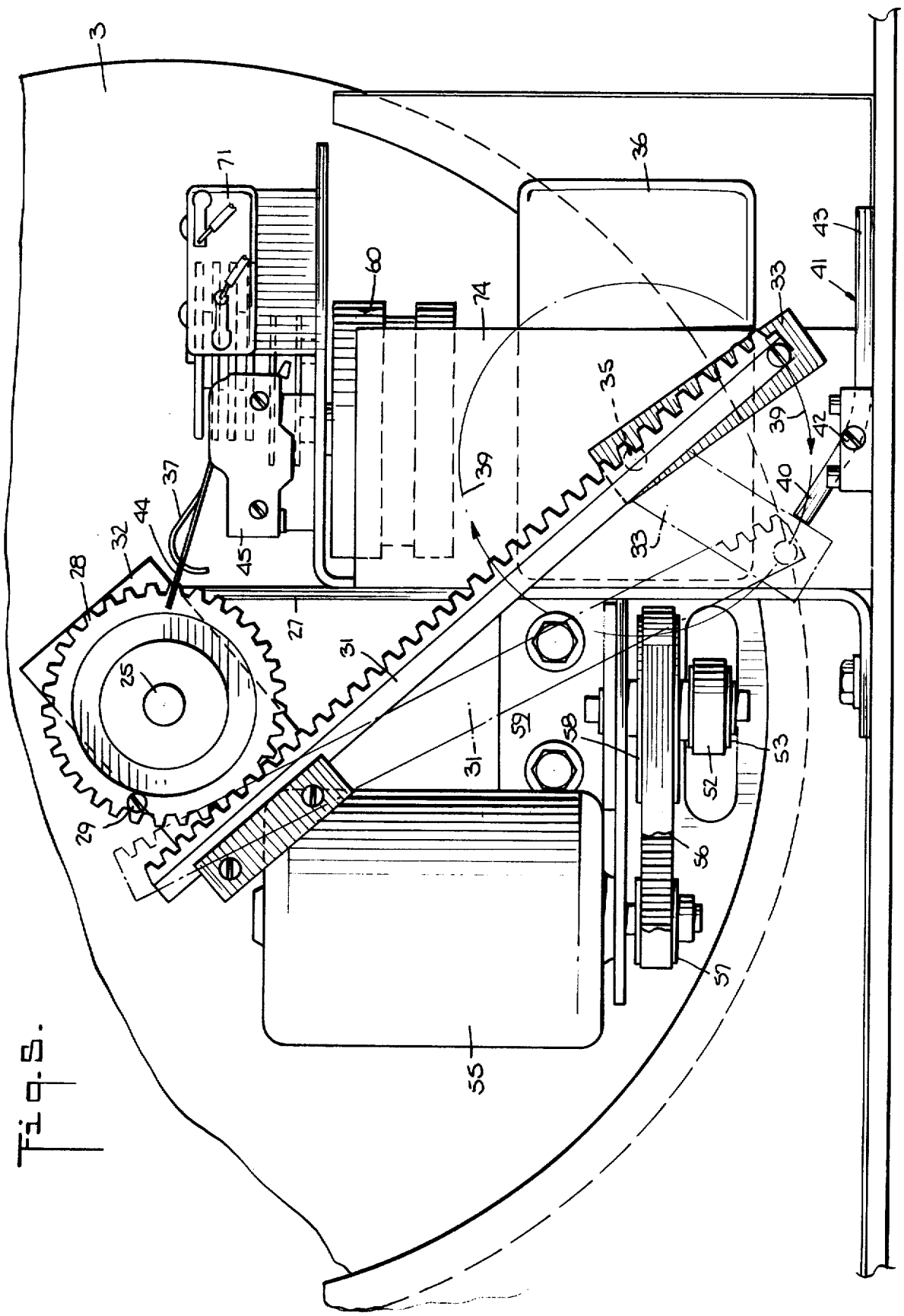

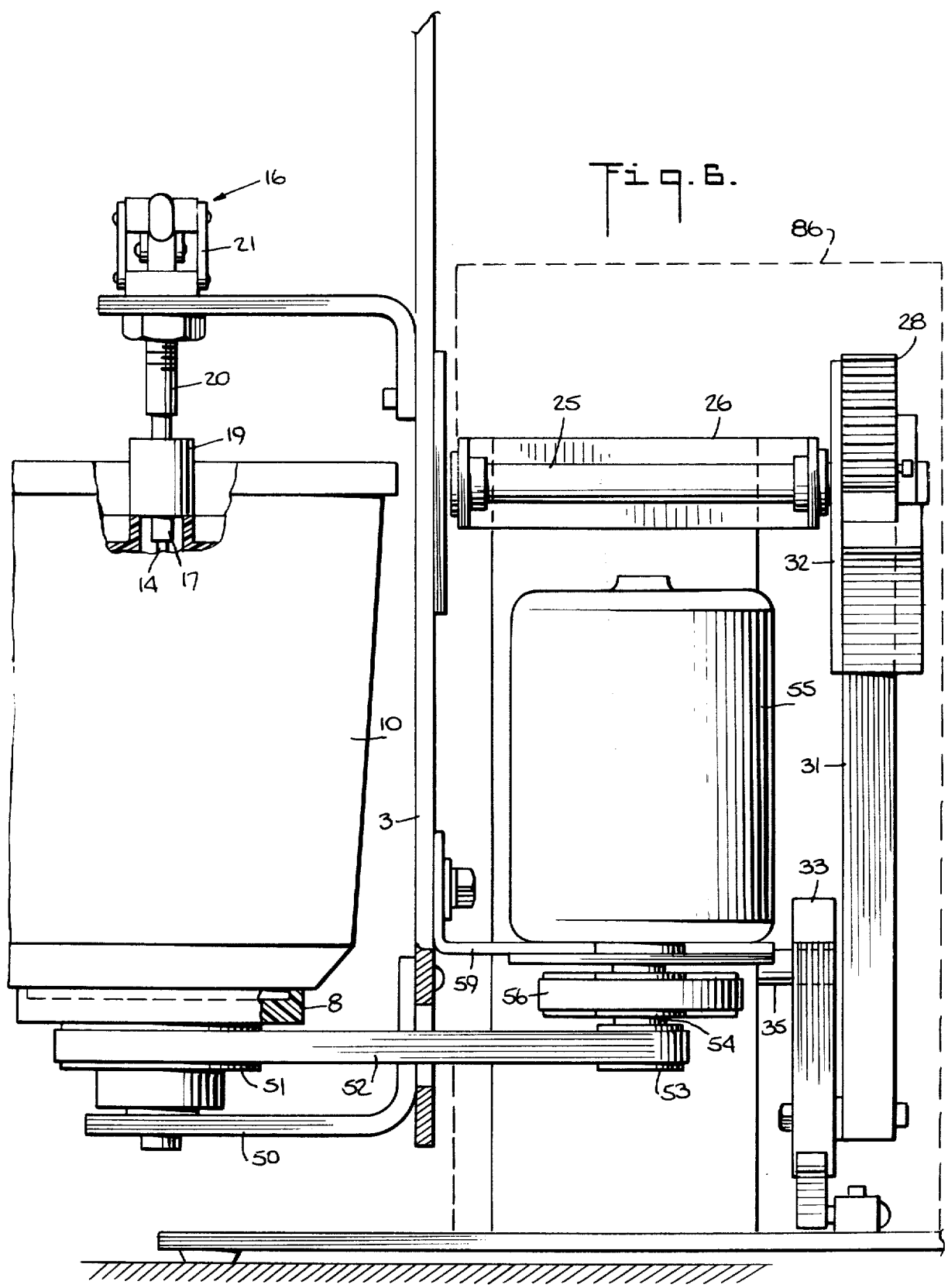

MACHINE FOR PREPARING ORTHOPEDIC CAST-MAKING MATERIALS

This is a continuation of application Ser. No. 536,243, filed Dec. 24, 1974.

This invention relates to a machine for tilting and rotating a container having resin-forming reactant liquids and a tape therein on which the liquids are to be coated, in a sequence and manner which will provide mixing of such liquids, impregnation of the tape with the resulting mixture and removal of the excess of the mixture from the tape.

In the co-pending application of Harold B. Kirkpatrick, Edward C. Distler and Marvin Menzin, Ser. No. 536,254, now abandoned, filed Dec. 24, 1974, entitled "PACKAGE AND METHOD FOR PREPARING ORTHOPEDIC CAST-MAKING MATERIALS," there is described a package having separated compartments at the bottom portion of the container, the compartments normally being sealed with respect to each other and one compartment containing a resin-forming reactant liquid and the other compartment containing a second resin-forming reactant liquid which reacts with the first liquid to form a resin, a cage-like spool removably mounted above the compartments for receiving an open weave, glass cloth tape, mixing paddles on the lower side walls of the container and a movable valve stem rod projecting from the top of the container whose downward movement activates the package by placing the compartments in communication with each other to thereby permit contact of the resin-forming liquids and initiate the forming of the resin. It is necessary to mix the liquids before applying them to the tape and, therefore, the mixing is performed in the bottom of the container by rotating it. Thereafter, the container is inverted to thereby cause the liquid mixture to enter the central portion of the tape spool. The container is again rotated at high speed in the inverted position to cause the liquid mixture to be centrifuged through the liquid-pervious tape. Thereafter, the container is returned to its upright position, in which it is again rotated at high speed to remove by extraction the excess of said mixture.

One object of the invention is to provide a machine which, when such a container is inserted therein, will place said compartments in communication with each other and thereafter automatically tilt and rotate such container in the sequence and for the required times, in order to cause the prescribed mixing, impregnating and excess mixture removal steps within such container.

In accordance with the preferred embodiment of the invention, the machine comprises a rotatable, normally horizontal platform for receiving the base of the container and such platform is rotatable by a first motor. The rotatable platform and the motor are mounted on a vertically disposed turntable which is rotatable around a horizontal axis substantially perpendicular to the axis of said rotatable platform. A vertically movable and latchable clamp is also mounted on the turntable in spaced relation to said platform and so that said container may be received between it and said platform. The turntable is rotatable by a second motor so that the container may be tilted, inverted and then returned to its upright position. The operation of the first and second motors is initiated and controlled in duration by a third, timing motor with its cams and switches, so as to produce rotation of said turntable and said platform in the prescribed sequence and for the desired times.

Other objects and advantages of the present invention will be apparent to those skilled in the art from the description of the presently preferred embodiment, which description should be considered in conjunction with the accompanying drawings in which:

FIG. 4 is a rear, perspective view of the machine of the invention;

FIG. 5 is an enlarged, fragmentary, rear view of the machine of the invention;

FIG. 6 is a fragmentary, side elevation view of the machine of the invention;

Figure 1:
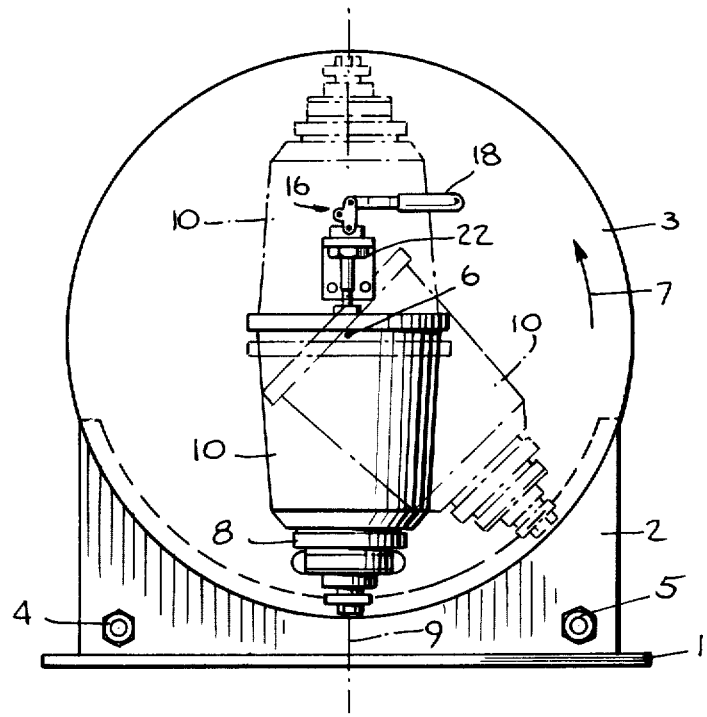
FIG. 1 is a schematic, front elevation view of the machine of the invention with a container held thereon.

With reference to FIG. 1, the preferred embodiment of the invention comprises a base 1 having mounted thereon a housing portion 2 and having rotatably mounted therefrom a turntable 3. An energizing switch 4 and an indicator lamp 5 are mounted on the housing portion 2.

Figure 3:
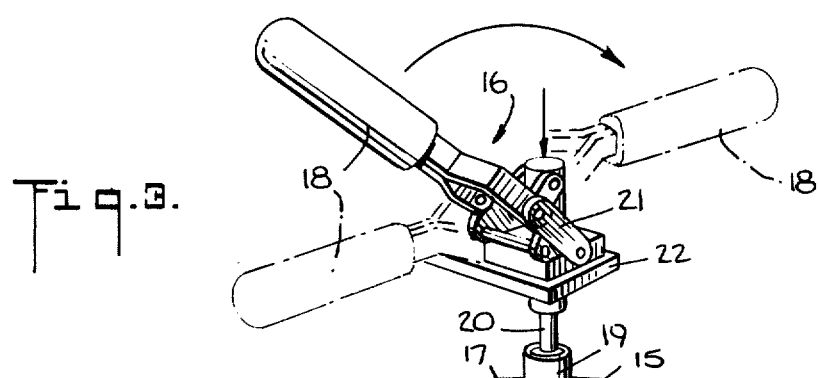
FIG. 3 is an enlarged, perspective view of the clamping means employed in the apparatus of the invention in association with the container.
Figure 2:
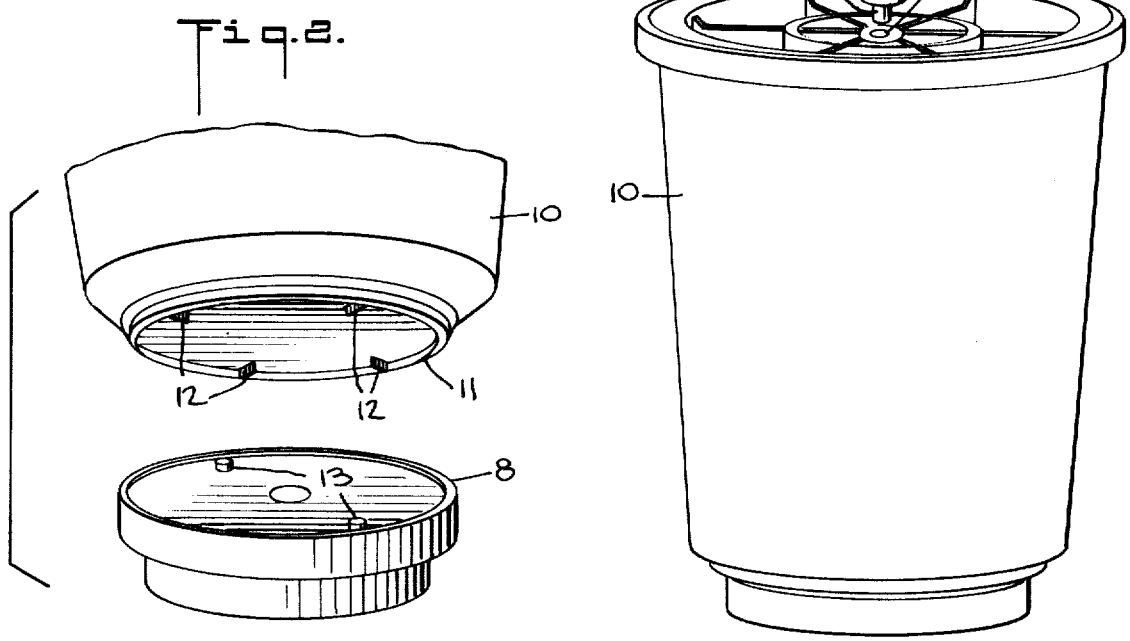
FIG. 2 is a fragmentary, enlarged view of the bottom of the container and the rotatable platform for supporting such container.

The turntable 3 is rotatable around a substantially horizontal axis 6 and, in the preferred embodiment as hereinafter described, is rotatable in the direction of the arrow 7. A container supporting platform 8 is rotatably mounted on the turntable 3 and is rotatable around an axis 9 which is substantially vertical when the turntable 3 is in the position shown. The platform 8 receives the base of a container 10 of the type described in said co-pending application. As illustrated in FIGS. 2 and 3, the base of the container 10 has a recessed portion 11 with inwardly extending tabs 12 which engageable with a pair of pins 13 on the platform 8, so as to assure rotation of the container 10 with the platform 8. The container 10 also has a central opening 15 through which projects the upper end of a valve stem or activator rod which, when depressed, causes opening of a sealed inner compartment within the container 10 which has a resin-forming liquid therein. When such compartment is opened by depressing the rod 14 (FIG. 6), the resin-forming liquid flows into the bottom portion of the container 10, which also has therein a resin-forming liquid which will react with the first-mentioned resin-forming liquid to form such resin within a short time, such as a few minutes.

A toggle action clamping means 16 is also mounted on the turntable 3 in a position such that the protruding portion 17 thereof will extend into the opening 15 when the clamp handle 18 is in the position indicated by dot-dash lines at the right in FIG. 3. The protruding portion 17 is secured to a collar 19 which is rotatably carried by a shaft 20. The shaft 20 is vertically movable toward and away from the container 10 by movement of the handle 18. Thus, when the handle 18 is in the position shown by dot-dash lines at the left of FIG. 3, the shaft 20 is fully raised, and when the handle 18 is in the position shown by dot-dash lines at the right of FIG. 3, the shaft 20 is fully depressed and by reason of the toggle linkages 21, the handle 18 is locked in the position at the right of FIG. 3, thereby locking the container 10 between the collar 19 and the platform 8. The toggle clamping mechanism 16 is of a well-known type and may, for example, be a toggle action clamp known as a De-Sta-Co clamp, manufactured and sold by De-Sta-Co Corporation, Detroit, Michigan. The mechanism 16 is supported from the turntable 3 by a bracket 22.

Accordingly, to insert a container in the machine of the invention, the handle 18 is moved to the left as viewed in FIGS. 1 and 3, the container 10 is placed with its base on the platform 8 and the handle 18 is then moved to the right thereby depressing the activator rod 14 and permitting one resin-forming material to flow into the bottom of the container 10 and contact the other resin-forming material in such bottom of the container. Such movement of the handle 18 also clamps the container between the collar 19 and the platform 8 so that when the platform 8 is subsequently rotated, the container 10 will rotate therewith.

With reference to FIGS. 4 and 5, the turntable 3 is secured to a shaft 25 which is rotatably supported by brackets 26 and 27, the axis of the shaft 25 being the same as the axis 6 identified hereinbefore. A gear 28, having a pin 29 extending axially therefrom, is secured to the shaft 25 so as to cause the shaft 25, and hence, the turntable 3, to rotate when the gear 28 is rotated.

The teeth of the gear 28 mesh with the teeth 30 of a linear rack 31, which is supported at one end from the shaft 25 by a plate 32, the plate 32 being pivotable with respect to the shaft 25. The opposite end of the rack 31 is pivotally connected to an arm 33 by means of a pin 34. The arm 33 at the end portion thereof opposite to the end portion thereof from which the pin 34 extends, is secured to the output shaft 35 of a first electric motor 36 so as to move with the shaft 35. FIG. 4 illustrates the parts in the position thereof when the turntable 3 is in the position shown in FIG. 1, and when the motor 36 is energized and the shaft 35 rotated in the clockwise direction, as indicated by the arrows 39 shown in FIG. 5, the arm 33 moves from the position shown in solid lines in FIG. 5 to the position shown in dot-dash lines in FIG. 5. As the arm 33 so moves, it moves the rack 31 from the position shown in solid lines in FIG. 5 to the position shown in dot-dash lines in FIG. 5, causing the gear 28, and hence, the shaft 25 and the turntable 3, to rotate. Preferably, the initial amount of such rotation is such as to tilt the axis of the container 10 to about 45° with respect to the vertical, as is shown by the so-tilted dot-dash outline of the container in FIG. 1.

As the arm 33 moves as described, it passes over the end 40 of a pivotally mounted stop 41 which lowers and permits the arm 33 to pass thereby in the clockwise direction. The stop 41 is pivotally mounted at 42 and has an arm 43 of greater weight than the balance thereof so as to return the stop 41 to the positions shown in FIGS. 4 and 5.

When the motor 36 has moved the arm 33 to a position in which it passes over the portion 43 of the stop 41, the plate 32 engages an arm 37 of a normally closed switch 38 and the motor 36 is de-energized, as described hereinafter. The gear 28, due to the weight of the container and supporting and rotating apparatus therefor, tends to turn counterclockwise, as viewed in FIG. 5, when the motor 36 is de-energized, and any significant movement of such gear 28 in the counterclockwise direction is prevented by engagement of the end 40 of the stop 41 with the arm 33. Thus, as long as the motor 36 remains de-energized, the turntable 3 will remain in the position in which the container 10 is at an angle of about 45° to the vertical, as shown in the tilted dot-dash outline in FIG. 1.

When the motor 36 is again energized as described hereinafter, the arm 33 continues to move in a clockwise direction further rotating the gear 28 in the clockwise direction, as viewed in FIGS. 4 and 5, until the pin 29 engages the arm 44 of a normally closed switch 45, at which time the motor 36 is again de-energized. The position of the arm 44 and the pin 29 are selected so that the motor 36 is de-energized when the container 10 reaches the inverted position shown by the dot-dash lines in FIG. 1.

When the motor 36 is again energized as described hereinafter, the arm 33 continues in the clockwise direction but after it becomes parallel to the rack 31, the arm 33 causes the rack 31 to rotate the gear 28 in the counterclockwise direction, as viewed in FIG. 5. Movement of the arm 33 continues until it reaches the position shown in solid lines in FIGS. 4 and 5, at which time the gear 28 will have rotated the turntable 3 until the container 10 is again in the upright position, as shown in solid lines in FIG. 1.

It will be noted from the foregoing, that by reason of the mechanisms described, the turntable 3 is moved through an angle of approxmiately 45° and then stops. Thereafter, it moves through a further angle equal to approximately 180° minus the angle of the initial movement and then stops. However, the turntable 3 does not make a full revolution and, instead, when it is again rotated it moves in the reverse direction for approximately 180°. As described hereinafter, the motor which rotates the platform 8 is mounted on the turntable 3 and while it would be possible to supply energizing current to such motor through suitable slip rings, it is desirable in the environment in which the machine is used to avoid, if possible, any electrical sparking. Accordingly, it is preferable to have wires extend directly to such motor for the rotating of the platform 8 and by means of the movement of the turntable 3, described hereinbefore, it is possible to supply the energizing current to the motor for the platform 8 without the use of slip rings.

With reference to FIGS. 5 and 6, the platform 8 is rotatably supported from a bracket 50 which is secured to the face of the turntable 3. The platform 8 is rotated by a pulley 51 engaged by a belt 52 which also engages a pulley 53 on a shaft 54 which, in turn, is driven by a second motor 55 through a belt 56 and a pair of pulleys 57 and 58. The motor 55 and its associated pulleys, etc. are supported from the back of the turntable 3 by a bracket 59.

When the motor 55 is energized, it rotates the platform 8, and hence, the container 10, and it will be observed that the motor 55 and its associated drive train are carried around the axis 6 by the turntable 3 as the latter is rotated by the motor 36.

The motors 36 and 55 are energized in their proper sequence by timing means comprising a motor 60 (FIGS. 5 and 7) which drives four cams 61, 62, 63 and 64 by means of a pair of pulleys 65 and 66 and a belt 67. The timing means also comprises a pair of switches 68 and 69 respectively operable by cams 61 and 64, and a pair of switches 70 and 71 respectively operable by cams 63 and 62. The switches 68–71, like the switches 38 and 45, may be of a type generally known as micro-switches. The motor 60, the cams 61–64 and the switches 38, 45 and 68–71 are supported by a plate 72 which is supported from the base 1 by brackets 27 and 74, the latter bracket also supporting the motor 36.

Figure 7:
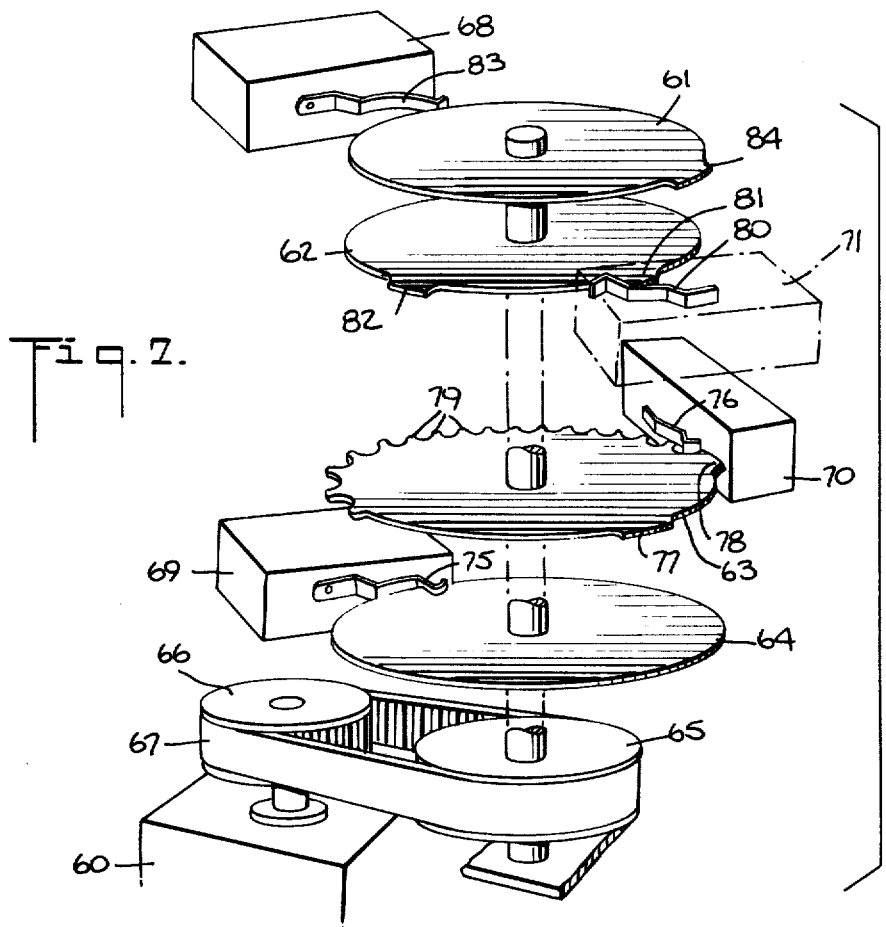
FIG. 7 is an exploded, perspective view of the timng means forming part of the machine of the invention.

The timing means is shown in greater detail in the exploded view of FIG. 7, in which it will be seen that the cam 64, which operates the switch 69, has a single recess for receiving an arm 75 of the switch 69, the switch 69 being a normally open switch. Accordingly, when the arm 75 is received in the recess of the cam 64, the switch 69 will be open.

The switch 70 also is a normally open switch and the actuating arm 76 thereof is engageable by projections 77, 78 and 79 thereon, the arm 76 when so engaged by a projection closing the switch 70.

The switch 71 is a normally open switch having an actuating arm 80 which closes the switch 71 when the arm 80 is engaged by either of the projections 81 and 82 on the cam 62. The switch 68 is a normally open switch having an actuating arm 83 which closes the switch 68 when it is engaged by the projection 84 on the cam 61.

Figure 8:
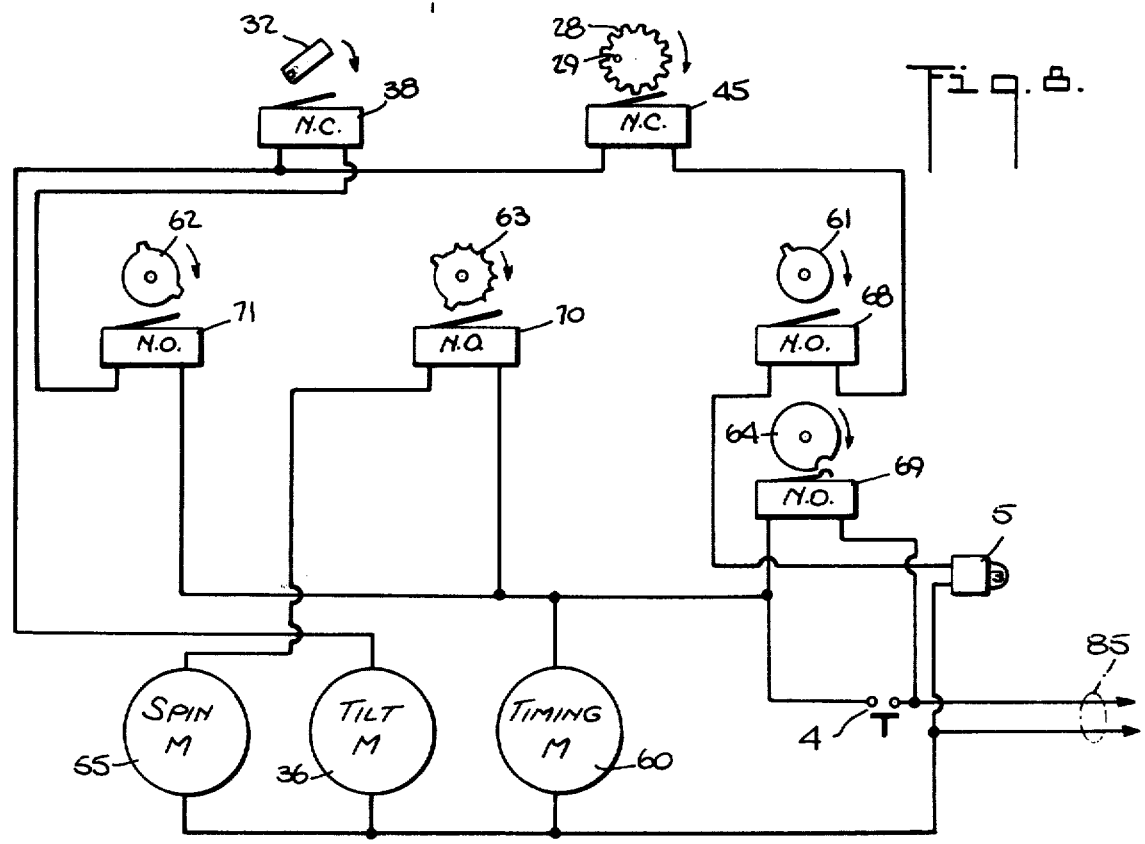
FIG. 8 is an electrical circuit diagram for the timing means and motors forming part of the machine of the invention.

FIG. 8 is an electrical circuit diagram of the machine of the invention, and it will be observed from FIG. 8 that when the switch 4 is closed, a circuit for the energization of the timing motor 60 is completed. The switch 4 must be held closed until the cam 64 has rotated sufficiently to close the switch 69 which will maintain the timing motor 60 energized until the cam 64 makes one revolution.

Shortly after the timing motor 60 is energized, the cam 62 closes the switch 71 completing a circuit from the supply lines 85 to the tilting motor 36 through the normally closed switch 38. When the turntable has been rotated by approximately 45°, the plate 32 opens the switch 38 thereby de-energizing the tilting motor 36. At this point, the cam 63 closes and opens the switch 70 a plurality of times, thereby energizing and de-energizing the motor 55 a plurality of times.

Thereafter, the cam 61 closes the switch 68 completing a circuit for the tilting motor 36 through the normally closed switch 45, and when the turntable 3 has been rotated approximately 180° from its initial position shown in FIG. 1, the pin 29 opens the switch 45, thereby de-energizing the tilting motor 36. The cam 63 then closes the switch 70 for a predetermined length of time, thereby energizing the motor 55 for such length of time.

When the motor 55 again becomes de-energized, the cam 62 again closes the switch 71 completing a circuit to the tilting motor 36 through the switch 38 which causes the tilting motor 36 to rotate the turntable 3 through approximately 180°.

When the turntable 3 has been returned to its initial position, the cam 63 again operates the switch 70 causing energization of the motor 55 for a predetermined length of time, and upon the expiration of such time, the motor 55 is de-energized, and the cam 64 permits the switch 69 to re-open, thereby opening the circuits of the various motors, etc. with respect to the supply lines 85.

The sequence of operations of the preferred embodiment of the machine of the invention is as follows:

1. After the container 10 has been clamped between the clamping means 16 and the platform 8 with the container 10 in the upright position as shown in solid lines in FIG. 1, the operator presses the button for the switch 4 and holds it for a short period of time. This causes the indicator lamp 5 to light and energizes the timing motor 60.

2. After the cam 64 has been rotated by the motor 60 through a small angle, the switch 69 is closed thereby maintaining the energization of the timing motor 60 and the operator may release the button of the switch 4.

3. After the cam 62 has been rotated by the motor 60 through a small angle, the projection 81 on the cam 62 closes the switch 71 thereby energizing the motor 36.

4. The motor 36 through the rack 31 and the gear 28 rotates the turntable 3 until the plate 32 operates the normally closed switch 38 and thereby de-energizes the motor 36, the turntable 3 then being at a position displaced by approximately 45° from the position shown in FIG. 1.

5. In the meantime, the cam 63 has rotated so that the switch 70 is about to be closed by one of the projections 79 to energize the motor 55. The motor 55 is then energized and de-energized several times by the projections 79 which close and open the switch 70. The number of projections 79 may be selected to accomplish the desired mixing.

6. After all the projections 79 on the cam 63 have passed the arm 76, the projection 84 on the cam 61 closes the switch 68 which re-energizes the motor 36 causing it, through the rack 31 and the gear 28, to again rotate the turntable 3 until the pin 29 on the gear 28 actuates the normally closed switch 45 to its open position, at which time the motor 36 is de-energized and the turntable 3 has been rotated 180° from the position shown in FIG. 1.

7. The projection 77 on the cam 63 then closes the switch 70 continuously energizing the motor 55 for a predetermined length of time to cause the mixture of resin-forming materials, which has been supplied to the core of the tape holding spool, due to inversion of the container 10, to flow outwardly by centrifugal action through the tape on the spool.

8. After the arm 76 of the switch 70 rides off the projection 77, the projection 81 on the cam 62 closes the switch 71, which re-energizes the motor 36 and causes it, through the rack 31 and the gear 28, to rotate the turntable 3 through approximately 180° and return it to the position shown in FIG. 1.

9. Shortly thereafter, the projection 78 on the cam 63 closes the switch 70 again energizing the motor 55 which spins the platform 8 and the container 10 thereby discharging excess resin-forming material from the tape by centrifugal action. The switch 70 is maintained closed for a predetermined length of time dependent upon the circumferential length of the projection 78 and then the switch 70 opens.

10. When the switch 70 opens, the arm 75 of the switch 69 is received in the recess on the arm 64 which disconnects various motors, etc. from the electrical supply line.

If desired, intermittent rotation of the platform 8 for mixing resin-forming materials may be performed with the container 10 in the upright position shown in FIG. 1, and, in this case, the switch 38 and its functions may be omitted. Also, the position of the cam 63 would be modified from that shown in FIG. 7 in an obvious manner, to cause intermittent energization of the motor 55 prior to energization of the motor 36 by the switch 71, the projection 81 on the cam 62 being omitted. Thus, the platform 8 and the container 10 would be intermittently rotated shortly after the button for the switch 4 is operated, and after the intermittent rotation of the platform 8 is discontinued, the switch 68 would be actuated to rotate the turntable 3 by 180°, as described hereinbefore. However, when the container 10 is in the upright position during the mixing, the mixture of resin-forming materials tends to have portions thereof cling to the side walls of the container 10, which is undesirable for proper mixing. In addition, if the volume of the resin-forming material is relatively small, the mixing is not as thorough as desired, and therefore, it is preferred that the container 10 be tilted to an angle of approximately 45° before the motor 55 is intermittently energized for mixing purposes.

In one embodiment of the invention, the timing motor 60 and the drive which interconnects it with the cams 61–64 was selected so that each cam made one revolution in one minute, thereby requiring one minute for the full cycle of operation. However, it will be apparent that the cycle of operation may be greater or less than one minute by suitably selecting the motor 60 and the means interconnecting it with the cams 61–64. Also, instead of continuously spinning the platform 8 when it is inverted, the projection 77 may be a plurality of projections, like the projections 79, to intermittently spin the platform 8 a plurality of times. In other words, the speed of rotation of the cams 61–64 and the shape and positions of the projections thereon may be selected to provide the timing and operations required to mix the resin-forming materials, impregnate or wet the tape therewith and remove any excess of the mixture.

Although in the embodiment described the circuits have been arranged to energize the motors themselves, i.e., by connecting them to the electrical source, it will be apparent to those skilled in the art that the motors 36 and 55 may be energized by the switch 69 and remain in continuous operation if they are connected to the parts which they drive through well-known electrical clutches which would be energized in lieu of energization of the motors 36 and 55 as described hereinbefore. Also, although the embodiment of the invention described has one motor 36 for rotating the turntable 3 and a second motor 55 for rotating the platform 8, the motor 36 may be omitted and the platform 8 and the turntable 3 may be rotated by the motor 55 using a known type of drive between the motor 55 and the turntable 3 for producing rotation of the turntable 3. However, in the event of the latter modification, it will be apparent that the motor 55 would drive the platform 8 and the turntable 3 through electrically operable clutches, which will be energized by the cams 61–64 and their associated switches in an obvious manner to accomplish the desired sequence of operations described hereinbefore.

Preferably, the various parts to the back of the turntable 3 are enclosed by a housing as indicated by the dot-dash lines 86 in FIG. 6.

Although in the embodiment illustrated the platform 8 and the clamping means 16 are disposed so that the axis 6 of the turntable 3 passes through the top portion of the container 10, it will be apparent that they may be differently disposed, e.g., with the axis 6 passing through the center of the container 10 or passing to one side of the container 10.

Although a preferred embodiment of the present invention has been illustrated and described, it will be apparent to those skilled in the art that various modifications may be made without departing from the principles of the invention.

What is claimed is:

1. A machine for tilting and rotating a container comprising a first support mounted for rotation around a predetermined, horizontal axis, a second support normally facing in an upward direction for receiving said container in the upright position thereof and rotatably mounted on said first support with its axis of rotation extending transversely to said first-mentioned axis, clamping means mounted on one of said supports for securing said container to said second support for rotation therewith, and rotating means including timing means, said rotating means being connected to said first and second supports for selected sequential and intermittent rotation of said first and second supports about their respective axes, said first support being rotatable by said rotating means for repositioning said second support from facing in the upward direction to a position in which it faces in a downward direction.

2. A machine as set forth in claim 1, wherein said rotating means includes reversible means for rotating said first support around its axis, said rotating means rotating said first support in a first direction around its axis in repositioning said second support from facing in an upward direction to said position in which said second support faces in a downward direction and, thereafter, rotating said first support in a second, opposite direction around its axis to a position in which said second support faces in an upward direction.

3. A machine as set forth in claim 1, wherein said rotating means sequentially (a) rotates said second support and then stops the rotation thereof, (b) rotates said first support until said second support faces in said downward direction, (c) again rotates said second support and then stops the rotation thereof, (d) rotates said first support until said second support faces in an upward direction, and (e) again rotates said second support and then stops the rotation thereof.

4. A machine as set forth in claim 1, wherein said rotating means comprises motor means driving said timing means, said timing means comprising rotatable cam means, second motor means mounted on said first support and connected to said second support for rotating the latter on its axis, and means including switch means between said timing cam means and said second motor means for actuating and deactuating the latter responsive to rotation of said cam means.

5. A machine as set forth in claim 1, wherein said rotating means comprises motor means including means connecting said motor means to said first support for imparting selected intermittent rotation to the latter on its said axis, and second motor means mounted on said first support and connected to said second support for rotating the latter on its said axis, and said timing means comprises rotatable cam means and means including switch means actuated upon rotation of said cam means and connected to said second motor means for imparting selected intermittent rotation to said second support.

6. A machine for tilting and rotating a container comprising a first support mounted for rotation around a predetermined, horizontal axis, a second support normally in a position in which it faces in an upward direction for receiving said container in the upright position thereof and rotatably mounted on said first support with its axis of rotation extending transversely to said first-mentioned axis, clamping means mounted on said first support in spaced relation to said second support for rotatably securing said container between said clamping means and said second support, motor means including means connecting said motor means to said first and second supports for independently rotating each of them about their respective axes, and timing means connected to said motor means for sequentially (a) causing said motor means to rotate said second support, (b) causing said motor to rotate said first support until said second support faces in a downward direction, (c) causing said motor means to rotate said second support while said second support faces in the downward direction, (d) causing said motor means to rotate said first support to reposition said second support until it faces in an upward direction and (e) causing said motor means to rotate said second support.

7. A machine as set forth in claim 6, wherein said timing means first causes said motor means to rotate said first support and thereby move said second support to a predetermined position at an angle less than 90° from said position in which it faces in an upward direction and then causes said motor means to rotate said second support intermittently and a plurality of times while said second support is in said predetermined position.

8. A machine as set forth in claim 7, wherein said motor means comprises a first motor connected by said connecting means to said first support for rotating the latter, a second motor mounted on said first support and connected by said connecting means to said second support for rotating the latter and said timing means comprises a third motor, cams driven by said third motor and switches operable by said cams, said switches being connected to said first and second motors and thereby respectively causing rotation of said first and second supports.

9. A machine as set forth in claim 8, wherein said first motor comprises a rotatable output shaft, and said connecting means connecting said first motor to said first support comprises a gear rotatable with said first support, a linear rack engaging said gear and means on said shaft spaced from the axis thereof and pivotally connected to said rack for oscillating said rack and causing at least longitudinal movement thereof.

10. A machine for tilting, rotating and inverting a container comprising a first support mounted for rotation on a predetermined axis, first motor means connected to said first support for rotating the latter on its said axis, a second support for receiving said container rotatably mounted on said first support with its axis of rotation extending transversely to said first-mentioned axis, second motor means mounted on said first support and connected to said second support for rotating the latter on its said axis, clamping means mounted on said first support in spaced relation to said second support for rotatably securing said container between said clamping means and said second support, and timing means connected to said first and second motor means for sequentially (a) operating said first motor means for the time required to rotate said first support through an angle less than 90°, (b) intermittently operating said second motor means a plurality of times to spin said second support a plurality of times, (c) operating said first motor means for the time required to rotate said first support through an angle substantially equal to 180° minus said first-mentioned angle, (d) operating said second motor means for a predetermined time to spin said second support, (e) operating said first motor means for the time required to rotate said first support through an angle substantially equal to 180° and (f) operating said second motor means for a predetermined time to spin said second support.

11. A machine as set forth in claim 10, wherein said first motor has a rotatable output shaft and said first motor is connected to said first support by rack and gear means comprising a gear on said first support rotatable therewith, a rack engaging said gear, driving means on said shaft rotatable therewith and means spaced from the axis of said shaft pivotally connecting said driving means to said rack for oscillating said rack and causing at least longitudinal movement thereof.

12. A machine as set forth in claim 11, wherein said timing means comprise a third motor, a plurality of cams driven by said third motor and a plurality of switches having actuating means operable by said cams, and further comprising a pair of switches having actuating means, means connecting said pair of switches electrically in series with said first motor and means mounting said pair of switches with the actuating means thereof in the path of movement of said rack and gear means for operating one of said pair of switches in a first predetermined position of said rack and gear means and the other of said pair of switches in a second predetermined position of said rack and gear means.

13. A machine as set forth in claim 10, wherein said timing means comprises a third motor, a plurality of cam driven by said third motor and a plurality of switches having actuating operable by said cams, means connecting at least one of said switches electrically in series with said first motor and means connecting at least one of said switches electrically in series with said second motor.

* * * * *

UNITED STATES PATENT AND TRADEMARK OFFICE
CERTIFICATE OF CORRECTION

PATENT NO. : 4,004,784
DATED : January 25, 1977
INVENTOR(S) : Edward C. Distler

It is certified that error appears in the above–identified patent and that said Letters Patent are hereby corrected as shown below:

Column 2, line 22, correct spelling of last word "timing";

Column 2, line 45, after word "which" and before word "engageable", insert the word --are--;

Column 6, line 57, after "the" (second occurrence) and before numeral "64", change "arm" to --cam--;

Column 10, line 17, change "(c)" to --(e)--;

Column 10, line 47, change first word "cam" to --cams--;

Column 10, line 48, after the word "actuating" and before word "operable", insert --means--.

Signed and Sealed this

Third Day of May 1977

[SEAL]

Attest:

RUTH C. MASON
*Attesting Officer*

C. MARSHALL DANN
*Commissioner of Patents and Trademarks*